United States Patent [19]

Peglion et al.

[11] Patent Number: 5,565,457
[45] Date of Patent: Oct. 15, 1996

[54] SUBSTITUTED SULFONAMIDES

[75] Inventors: Jean-Louis Peglion, Le Vesinet;
Jean-Paul Vilaine, Chatenay Malabry;
Nicole Villeneuve, Rueil Malmaison;
Jean-Pierre Iliou, Puteaux;
Jean-Pierre Bidouard, Chilly Mazarin, all of France

[73] Assignee: Adir et Compagnie, Courbevoie, France

[21] Appl. No.: 393,452

[22] Filed: Feb. 23, 1995

[51] Int. Cl.$^6$ ............... A61K 31/495; C07D 401/00; C07D 413/00; C07D 241/04

[52] U.S. Cl. ............... 514/253; 514/252; 544/363; 544/364; 544/368; 544/376; 544/380

[58] Field of Search ............... 544/363, 364, 544/368, 376, 380; 514/252, 253

[56] References Cited

U.S. PATENT DOCUMENTS 4,948,892  8/1990  Tanabe et al. ............... 544/398
5,326,870  7/1994  Kajihara et al. ............... 540/575

FOREIGN PATENT DOCUMENTS 330065  8/1989  European Pat. Off. ............... 544/398
14712   9/1992  WIPO ............... 544/398

*Primary Examiner*—Cecilia Tsang
*Attorney, Agent, or Firm*—The Firm of Gordon W. Hueschen

[57] ABSTRACT

The compounds are N-(2,3,4-trimethoxybenzyl)piperazines N'-substituted by a radical containing a sulfonamide group, and pharmaceutically tolerable salts thereof, useful for treating myocardial ischaemic pathologies, cerebral vascular accident and manifestations of deficiency associated with chronic cerebral circulatory disorders.

A compound disclosed is : N-benzyl-N-{3,3-dimethyl-4-[4-(2,3,4-trimethoxybenzyl) piperazin-1-yl]butyl}-(isoquinolin-5-yl)sulfonamide and its fumarate.

12 Claims, No Drawings

SUBSTITUTED SULFONAMIDES

The present invention relates to new substituted sulfonamides, a process for their preparation and pharmaceutical compositions containing them.

It relates more especially to:
substituted sulfonamides of formula I:

$$A-\underset{\underset{O}{\overset{O}{\|}}}{\overset{\|}{S}}-\underset{R_1}{\overset{|}{N}}-D-N\underset{\underline{\qquad}}{\overline{\qquad}}N-CH_2-\text{[2,3,4-trimethoxyphenyl]} \quad (I)$$

wherein:
A represents a radical of formula:

[isoquinoline, benzoxadiazole, benzothiadiazole, chromone structures]

[bicyclic CH₂-substituted structures with =O, OH, or OH/CH₂-COOH]

$R_1$ represents:
a) a hydrogen atom,
b) a straight-chain alkyl radical containing from 1 to 7 carbon atoms and optionally substituted by one or more methyl, phenyl, pyridyl or thienyl radicals, which are themselves optionally substituted either by one or more halogen atoms or by a hydroxy radical,
c) an alkenyl radical containing from 3 to 7 carbon atoms (such as, for example, $-CH_2-CH=CH_2$), or
d) an alkynyl radical containing from 3 to 7 carbon atoms (such as, for example, $-CH_2-C\equiv CH$); and D represents:
a) a saturated linear hydrocarbon chain containing from 2 to 6 carbon atoms that is interrupted by one or more oxygen or sulphur atoms or by a cyclopropane ring or is substituted by a gem-dimethyl, or
b) a group of formula:

$-CH_2-\text{[phenyl]}$, $-CH_2-\text{[phenyl]}-CH_2-$, or $-H_2C-\text{[pyridyl]}-CH_2-$ and also their physiologically tolerable addition salts with appropriate acids.

The closest prior art to the present invention is illustrated by the European 2Patent Application published under the number 0 330 065 A, which relates to sulfonamides of formula:

$$R_1,R_2,R_3\text{-[phenyl]}-SO_2-\underset{R_4}{\overset{|}{N}}-(CH_2)_n-N\underset{\underline{\qquad}}{\overline{\qquad}}N-R_5,$$

that is to say compounds in which the sulfonamide function is always attached to a benzene ring that is itself optionally substituted, but the Application does not include or suggest at all bicyclic radicals of formula A as defined for formula I described above.

Consequently, the reference EP 0 330 065 A cannot influence the patentability of the present Application.

The present invention relates also to a process for the preparation of compounds of formula I which is characterised in that a sulfochloride of formula II:

$$A-SO_2Cl \quad (II)$$

wherein A is as defined above,
is reacted with an amine of formula III:

$$HN(R_1)-D-N\underset{\underline{\qquad}}{\overline{\qquad}}N-CH_2-\text{[2,3,4-trimethoxyphenyl]} \quad (III)$$

wherein $R_1$ and D are as defined above.

Moreover, compounds of formula I wherein $R_1$ has the meanings given above with the exception of hydrogen, that is to say compounds corresponding to formula I':

$$A-SO_2-\underset{R_1'}{\overset{|}{N}}-D-N\underset{\underline{\qquad}}{\overline{\qquad}}N-CH_2-\text{[2,3,4-trimethoxyphenyl]} \quad (I')$$

wherein:
A and D are as defined above and $R'_1$ represents:
α) a straight-chain alkyl radical containing from 1 to 7 carbon atoms and optionally substituted by one or more methyl, phenyl, pyridyl or thienyl radicals, which are themselves optionally substituted either by one or more halogen atoms or by a hydroxy radical,
β) an alkenyl radical containing from 3 to 7 carbon atoms (such as, for example, $-CH_2-CH=CH_2$), or
χ) an alkynyl radical containing from 3 to 7 carbon atoms (such as, for example, $-CH_2-C\equiv CH$);

may also be prepared by reacting compounds of formula I wherein $R_1$ is a hydrogen atom only, that is to say by reacting compounds of formula I":

$$A-SO_2-\underset{H}{\overset{|}{N}}-D-N\underset{\underline{\qquad}}{\overline{\qquad}}N-CH_2-\text{[2,3,4-trimethoxyphenyl]} \quad (I'')$$

wherein A and D are as defined above,
with sodium hydride then a halide of formula II':

$$R'_1X \quad (II')$$

wherein $R'_1$ is as defined above and X represents a halogen atom, in an appropriate solvent, such as N,N-dimethylacetamide.

The compounds of formula I may be convened into addition salts with physiologically tolerable acids, which salts, as such, form part of the invention. There may be mentioned as acids that can be used for the formation of those salts, for example, in the mineral series hydrochloric, hydrobromic, nitric, sulfuric and phosphoric acid and, in the organic series, acetic, propionic, maleic, fumaric, tartaric, oxalic, benzoic, methanesulphonic and isethionic acid.

All the sulfochlorides of formula II used as starting materials are described in the literature. The starting materials of formula III were prepared from known products by various methods depending on the meanings of D and $R_1$, as mentioned in the Examples which follow.

The compounds of the present invention have valuable pharmacological and therapeutic properties. In particular, the following has been demonstrated for those compounds:

IN VITRO on the one hand:
their antihypoxic activity, which prevents the dysfunction of isolated rats' hearts in the course of hypoxia-reoxygenation protocols and limits the necrosis of cardiac cells induced by hypoxia on the other hand:
their protecting capacity in respect of an excess intracellular calcium model : against the necrosis of rat cardiac cells induced by calcium paradox; and

IN VIVO their anti-ischaemic activity in the course of myocardial ischaemia protocols induced by coronary stenosis in pigs.

Those properties allow the compounds of the present invention to be used as medicaments in the preventative or curative treatment of ischaemic pathologies, especially in the cardiovascular field: angina pectoris, myocardial infarction and the sequelae of ischaemic cardiopathies (rhythm disorder, cardiac insufficiency) and of peripheral vascular pathology.

The compounds of the present invention may also be used in the cerebral field, especially in the treatment of cerebral vascular accident and the manifestations of deficiencies associated with chronic cerebral circulatory disorders; in the ophthalmology field : especially in the treatment of retina disorders of vascular origin; and in neurosensory manifestations of ischaemic origin.

The dosage may vary, especially in accordance with the age and weight of the patient, the route of administration, the nature of the disorder and associated treatments, and ranges from 1 to 200 mg of active ingredient from 1 to 3 times per day.

The present invention relates also to pharmaceutical compositions comprising as active ingredient a compound of formula I or a physiologically tolerable salt thereof, mixed with or in association with one or more appropriate pharmaceutical excipients.

The so-obtained pharmaceutical compositions are generally presented in dosage form comprising from 1 to 200 mg of active ingredient They may, for example, be in the form of tablets, dragées, gelatin capsules, suppositories or injectable or drinkable solutions, and may be administered by the oral, rectal or parenteral route depending on the case in question.

The following Examples illustrate the invention. Unless specified otherwise, the melting points are determined using a Kofler hot plate.

EXAMPLE 1

N-ethyl-N-{3,3-dimethyl-4-[4-(2,3,4-trimethoxybenzyl)-piperazin-1-yl]butyl}-(isoquinolin- 5-yl)sulfonamide:

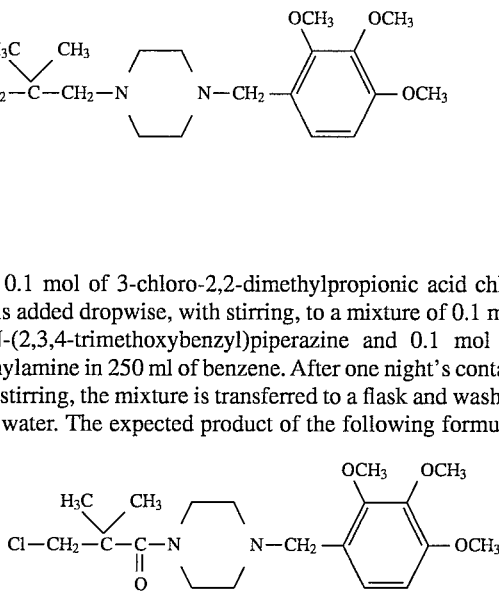

1) 0.1 mol of 3-chloro-2,2-dimethylpropionic acid chloride is added dropwise, with stirring, to a mixture of 0.1 mol of N-(2,3,4-trimethoxybenzyl)piperazine and 0.1 mol of triethylamine in 250 ml of benzene. After one night's contact with stirring, the mixture is transferred to a flask and washed with water. The expected product of the following formula:

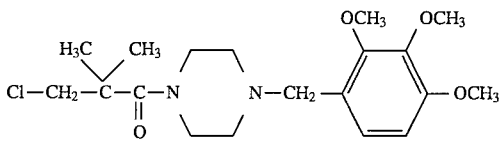

is separated off in the form of an oil in a yield of 54%.

2) 0.053 mol of the product so obtained and 0.063 mol of sodium iodide in 600 ml of methyl ethyl ketone are heated at reflux for 24 hours. After monitoring by HPLC, 0.063 mol of sodium iodide are added again, followed by refluxing for 24 hours. The whole is brought to room temperature, evaporated, taken up in ether, and washed with Normal sodium thiosulfate. The expected product of formula:

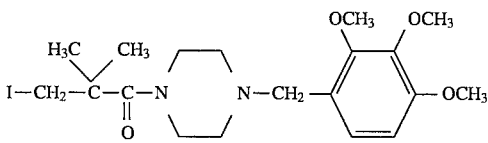

is obtained in the form of an oil in a yield of 95%.

3) The iodinated compound obtained above is heated at 100° C. for 6 hours,, with stirring, with two equivalents of sodium cyanide in 100 ml of dimethylformamide. The dimethylformamide is then evaporated off and the residue is taken up in water and extracted with diethyl ether. The nitrile so obtained, in a yield of 54% and in the form of an oil, is used as it is without further purification.

4) The nitrile obtained above is dissolved in 250 ml of tetrahydrofuran and the resulting solution is subjected to the action of 10 equivalents of borane-dimethyl sulfide. The reaction mixture is heated at reflux for 6 hours.

After solvolysis with 25 ml of methanol, followed by evaporation and hydrolysis with 40 ml of concentrated HCl in 80 ml of methanol, the whole is evaporated, taken up in water and extracted with diethyl ether and the aqueous phase is rendered basic and extracted with ethyl acetate. The expected amine is obtained in the form of an oil in a yield of 90%.

5) 0.017 mol of (isoquinolin-5-yl)sulfochloride hydrochloride is added in portions, at room temperature, to 0.017 mol of the amine obtained above and 0.034 mol of triethylamine in 65 ml of methylene chloride. The reactants are left in contact overnight, with stirring, then transferred to a flask and washed with 100 ml of Normal sodium hydroxide solution, and the organic phase is dried. Chromatography is then carried out in a $CH_2Cl_2/CH_3OH$ (95:5) system on a silica column, and 6.3 g of the expected product are collected in the form of an oil.

6) 2.8 g (0.005 mol) of the sulfonamide prepared in the preceding Step, dissolved in 30 ml of dimethyl acetamide, are reacted with a stoichiometric amount of 60% sodium hydride. When the evolution of gas has ceased, 0.005 mol of ethyl iodide is added and the reaction mixture is stirred overnight. The mixture is then diluted abundantly with water, extracted with ethyl acetate, dried and evaporated, yielding the title product of Example 1 in the form of an oil in a yield of 64%. The difumarate of N-ethyl-N-{3,3-dimethyl-4-[4-(2,3,4-trimethoxybenzyl)piperazin-1-yl]butyl}-(isoquinolin-5-yl)sulfonamide melts at 143°–146° C.

EXAMPLES 2 TO 5

The compounds forming the subject of the following Examples were prepared by proceeding analogously to the method described in Example 1:

2) N-benzyl-N-{3,3-dimethyl-4-[4-(2,3,4-trimethoxybenzyl)piperazin-1-yl]butyl}-(isoquinolin-5-yl)sulfonamide, m.p. of the corresponding 2,5-fumarate: 174°–176° C.

3) (1R)-N-ethyl-N-{3,3-dimethyl-4- [4-(2,3,4-trimethoxybenzyl) piperazin-1-yl]butyl}-10-camphosulfonamide, m.p. of the corresponding dihydrochloride: 243°–245° C.

4) (1S)-N-ethyl-N-{3,3- dimethyl-4-[4-(2,3,4-trimethoxybenzyl) piperazin-1-yl]butyl}-10-camphosulfonamide, m.p. of the corresponding dihydrochloride: 243°–245° C.

5) (1R)-N-benzyl-N-{3,3-dimethyl-4-[4-(2,3,4- trimethoxybenzyl) piperazin-1-yl]butyl}-10-camphosulfonamide, m.p. of the corresponding dihydrochloride: 188°–191° C.

EXAMPLE 6

N-benzyl-N-{[4-[4-(2,3,4-trimethoxybenzyl)piperazin-1-yl]phenyl]methyl}-(isoquinolin-5-yl) sulfonamide

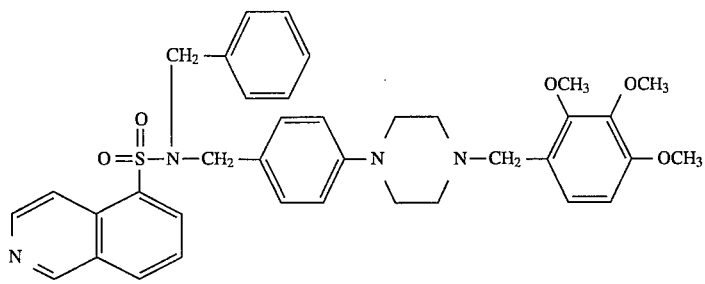

1) 0.2 mol of fluorobenzonitrile, 0.2 mol of potassium carbonate and 0.2 mol of N-(2,3,4-trimethoxybenzyl) piperazine are heated at 100° C. for 8 hours with stirring. The whole is then diluted with water and extracted with diethyl ether, the organic phase is extracted with Normal hydrochloric acid, and the combined aqueous phases are rendered basic, in the cold, with concentrated sodium hydroxide solution and extracted with ethyl acetate. The expected nitrile is obtained in the form of an oil in a yield of 40%.

2) The nitrile so obtained is reduced with one equivalent of lithium aluminium hydride in 150 ml of tetrahydrofuran. After decomposition, an oil is obtained which is subjected to flash chromatography using $CH_2Cl_2/CH_3OH/NH_4OH$ (95:5:0.5) as eluant. The expected amine is obtained in the form of an oil in a yield of 37%.

3) Coupling the amine obtained above with (isoquinolin-5-yl)sulfochloride is carried out in accordance with the method described in Example 1, paragraph 5). The N-alkylation is carried out by the method described in Example 1, paragraph 6) using benzyl bromide instead of ethyl iodide. In that manner the title product of Example 6, of which the hydrochloride melts at 152°–155° C., is obtained.

EXAMPLE 7

Cis-N-ethyl-N-{2-[4-(2,3,4-trimethoxybenzyl) piperazin-1-ylmethyl]cyclopropylnethyl}- (isoquinolin-5-yl)sulfonamide.

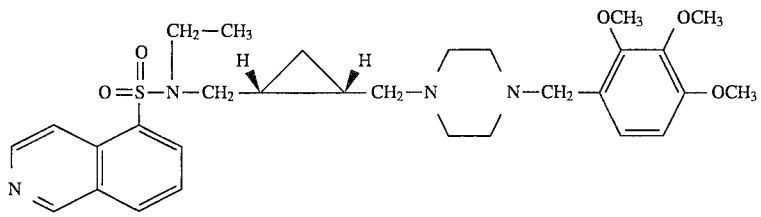

1) Preparation of the cis/trans mixture of methyl 2-cyanocycloprop-1-ylcarboxylate:

A mixture of 0.5 mol of acrylonitrile and 0.5 mol of methyl chloroacetate is poured onto a suspension of 50 ml of toluene and 0.5 mol of sodium hydride. The reaction mixture is left for one night with stirring, then decomposed very slowly with 150 ml of diethyl ether containing 16 ml of methanol. The whole is transferred to a flask, diluted with diethyl ether, washed with a saturated sodium chloride solution, dried and evaporated.

The cis/trans mixture is collected by distillation, B.p./$_{5\ mm}$=120°–140° C. (yield: 20%).

2) Preparation of the cis/trans mixture of 2- cyanocycloprop-1-ylcarboxylic acid:

11.7 g (0.093 mol) of the methyl 2-cyanocycloprop-1-ylcarboxylate obtained above are hydrolysed with 100 ml of Normal sodium hydroxide solution and 50 ml of ethanol, with stirring for one night. The alcohol is evaporated off, 100 ml of Normal hydrochloric acid are added and the whole is evaporated to dryness to a constant weight.

The precipitate is taken up in 100 ml of acetonitrile, the sodium chloride is filtered off and evaporation is carried out. The cis/trans mixture of 2-cyanocycloprop-1- ylcarboxylic acid is obtained, m.p.: 80°–90° C. (yield: 81%).

3) Preparation of 1-cyano-{2-[4-(2,3,4-trimethoxybenzyl)piperazin-1-yl]carbonyl}cyclopropane in separated cis and trans isomer forms:

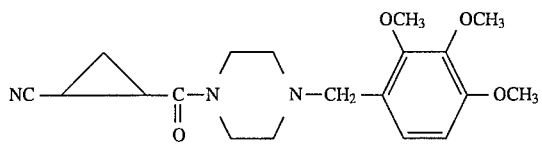

12.2 g (0.075 mol) of carbonyldiimidazole are added in one go to a suspension of 8.4 g (0.075 mol) of 2-cyanocycloprop-1-ylcarboxylic acid and 50 ml of CH$_2$Cl$_2$, and the whole is stirred for two hours after the evolution of gas has ceased. 20 g (0.075 mol) of 4-(2,3,4-trimethoxybenzyl)piperazine in 100 ml of CH$_2$Cl$_2$ are poured in dropwise and the whole is left for one night with stirring. The whole is then poured into a flask, washed with water, dried and evaporated. Flash chromatography yields 8.3 g (35%) of the trans isomer (oil) and 11.1 g (47%) of the cis isomer, m.p.: 108°–110° C.

4) Preparation of cis-2-{[4-(2,3,4-trimethoxybenzyl) piperazin-1-yl]methyl} cycloprop-1-ylmethylamine:

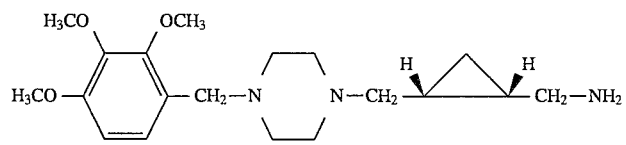

22.7 g (0.3 mol) of borane-dimethyl sulfide are poured dropwise onto a stirred solution of 8.3 g of the cis- nitrile obtained beforehand in 315 ml of tetrahydrofuran. The whole is heated at reflux for 6 hours, returned to room temperature, slowly decomposed with 20 ml of methanol and maintained at reflux until the evolution of gas has ceased. Subsequently, the whole is evaporated, taken up in 50 ml of methanol and 10 ml of concentrated hydrochloric acid, and heated at reflux until the evolution of gas has ceased.

The methanol is then evaporated off and the aqueous phase is rendered basic in the cold, extracted with diethyl ether, dried and evaporated. Yield: 2.3 g (29%).

5) Preparation of the cis-compound of formula:

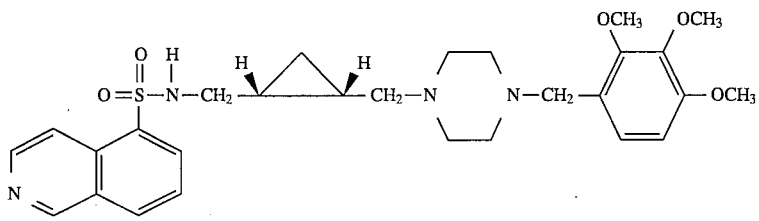

1.1 g (0.004 mol) of (isoquinolin-5-yl)sulfochloride hydrochloride are added in portions to a solution of 2.3 g (0.008 mol) of cis-{{2-[4-(2,3,4-trimethoxybenzyl)piperazin-1-yl]methyl} cycloprop-1-yl}methylamine and 0.8 g of triethylamine in 25 ml of $CH_2Cl_2$. The reactants are left in contact for one night then transferred to a flask, washed with Normal sodium hydroxide solution, then with water, and evaporated. Flash chromatography using $CH_2Cl_2/CH_3OH$ (95:5) as eluant yields 1.2 g of the expected product in a yield of 57%.

6) Preparation of the title compound of Example 7:

1.2 g (0.0024 mol) of the sulfonamide obtained in 5) in 15 ml of dimethyl acetamide is treated with 0.1 g of 60% sodium hydride. Subsequently 0.4 g of ethyl iodide is added and the mixture is left at room temperature for the night with sing. The whole is diluted with water and extracted with ethyl acetate. Flash chromatography using $CH_2Cl_2/CH_3OH$ (95:5) as eluant yields 1 g of the desired substance (yield: 80%). The salt formation is carded out by dissolving in 5 ml of ethyl acetate to which 3 equivalents of N HCl in diethyl ether are added. The whole is filtered and dried and the product is crystallised in 5 ml of methyl cyanide, giving cis-N-ethyl-N-{2-[4-( 2,3,4-trimethoxybenzyl) piperazin-1-ylmethyl]cyclopropylmethyl}-(isoquinolin-5-yl)sulfonamide trihydrochloride, m.p.: 175° C.

EXAMPLE 8

Trans-N-ethyl-N-{2-[4-(2,3,4-trimethoxybenzyl) piperazin-1-ylmethyl]cyclopropylmethyl}- (isoquinolin-5-yl)sulfonamide:

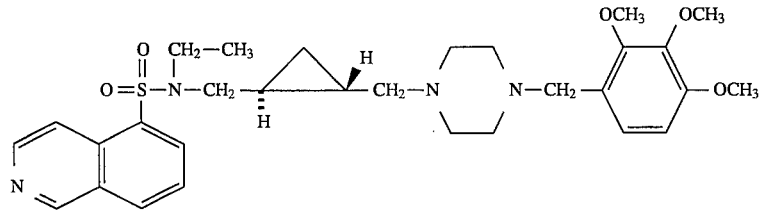

was prepared analogously to the method described in Example 7 but, starting from paragraph 4), with replacement of the cis compound by the corresponding trans compound.

The trihydrochloride of the title product of Example 8 melts at 162°–165° C.

EXAMPLE 9

Cis-N-benzyl-N-{2-[4-(2,3,4-trimethoxybenzyl) piperazin-1-ylmethyl]cyclopropylmethyl}- (isoquinolin-5-yl)sulfonamide:

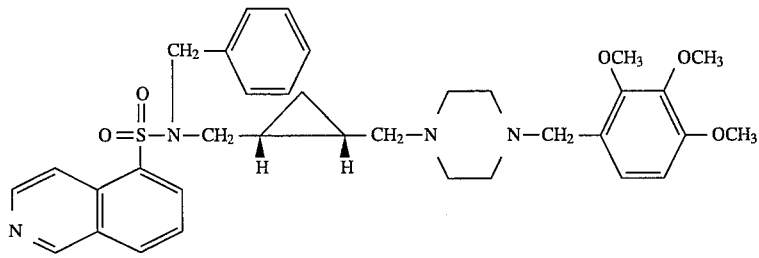

was prepared as indicated in Example 7, but with replacement of the ethyl iodide in paragraph 6) by benzyl bromide.

The trihydrochloride of cis-N-benzyl-N-{2-[4-(2,3,4- trimethoxybenzyl)piperazin-1-ylmethyl]cyclopropylmethyl}- (isoquinolin-5-yl)sulfonamide is thereby obtained, m.p. 202°–204° C.

EXAMPLE 10

N-(pyrid-3-ylmethyl)-N-{3,3-dimethyl-4-[4-(2,3,4-trimethoxybenzyl) piperazin-1-yl]butyl}-(isoquinolin-5-yl) sulfonamide:

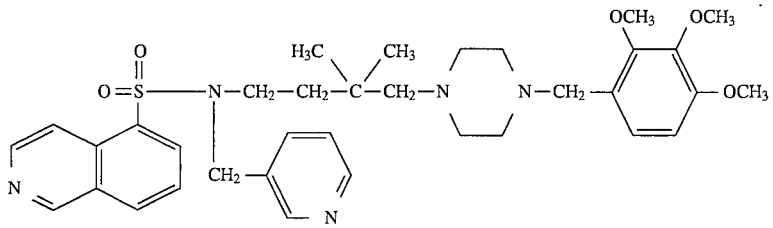

1) Preparation of the amine of formula:

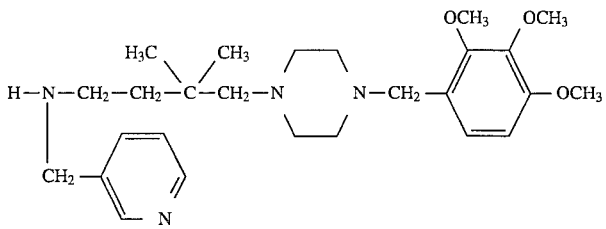

7.3 g (0.02 mol) of the amine obtained in paragraph 4) of Example 1 are heated to reflux, in 80 ml of ethanol, with 2.14 g (0.02 mol) of 3-pyridinecarbonaldehyde. After the mixture has returned to room temperature, 0.8 g of sodium borohydride is added in portions. The reactants are left in contact for 4 hours after the evolution of gas has ceased, then diluted with water and extracted with diethyl ether. After drying and evaporation, 6.5 g of an oil are obtained of which the characteristics correspond to the expected product and which is used as such without further purification.

2) Preparation of the title compound of Example 10:

The amine obtained above is condensed with (isoquinolin-5-yl)sulfochloride hydrochloride in accordance with the method described in Example 1, paragraph 5), to obtain the title compound of Example 10 of which the tetrahydrochloride melts at a temperature higher than 260° C.

EXAMPLES 11 TO 14

The compounds forming the subject of the following Examples were prepared by proceeding in accordance with the method described in Example 10:

11) N-(pyrid-2-ylmethyl)-N-{3,3-dimethyl-4-[4-(2,3,4-trimethoxybenzyl) piperazin-1-yl]butyl}-(isoquinolin-5-yl)sulfonamide, with replacement of the 3-pyridinecarbonaldehyde in paragraph 1) of Example 10 by 2-pyridinecarbonaldehyde. The free base obtained melts at 110°–113° C.

12) N-(pyrid-4-ylmethyl)-N-{3,3-dimethyl-4-[4-(2,3,4-trimethoxybenzyl) piperazin-1-yl]butyl}-(isoquinolin-5-yl)sulfonamide, with replacement of the 3-pyridinecarbonaldehyde in paragraph 1) of Example 10 by 4-pyridinecarbonaldehyde. The tetramethanesulfonate of the title product melts at 143°–146° C.

13) N-(thien-2-ylmethyl)-N-{3,3-dimethyl-4-[4-(2,3,4-trimethoxybenzyl) piperazin-1-yl]butyl}-(isoquinolin-5-yl)sulfonamide, with replacement of the 3-pyridinecarbonaldehyde in paragraph 1 of Example 10 by 2-thiophenecarbonaldehyde. The trihydrochloride of the title product melts at 188°–190° C.

14) N-(thien-3-ylmethyl)-N-{3,3-dimethyl-4-[4-(2,3,4-trimethoxybenzyl) piperazin-1-yl]butyl}-(isoquinolin-5-yl)sulfonamide, with replacement of the 3-pyridinecarbonaldehyde in paragraph 1) of Example 10 by 3-thiophenecarbonaldehyde.

The trihydrochloride of the title product melts at 158°–160° C.

EXAMPLE 15

N-ethyl-N-{{4-[4-(2,3,4-trimethoxybenzyl)piperazin-1-yl]methyl}benzyl}-(isoquinolin-5-yl)sulfonamide:

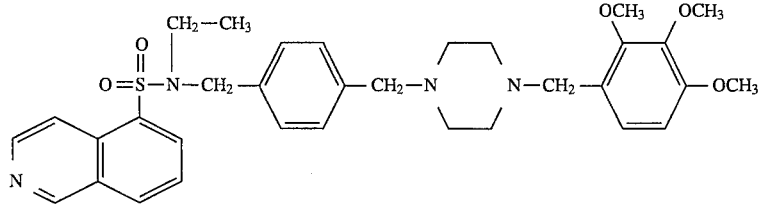

1) Preparation of the nitrile of formula:

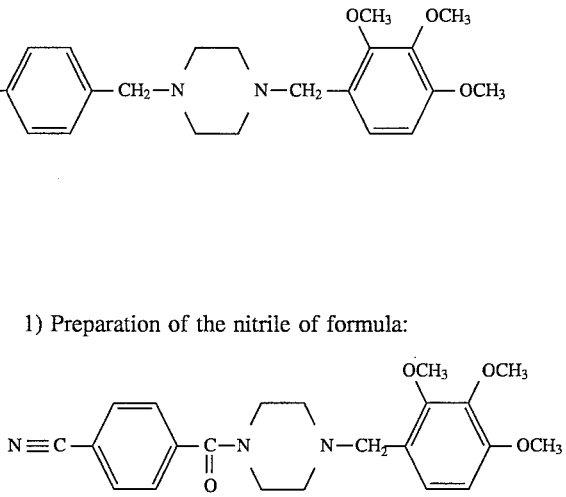

27.6 g (0.17 mol) of carbonyldiimidazole are added to a suspension of 25 g (0.17 mol) of p-cyanobenzoic acid in 250 ml of methylene chloride.

When the evolution of gas has ceased, the reactants are left in contact for a further 2 hours. There are then rapidly added dropwise to the resulting solution 45.3 g (0.17 mol) of 1-(2,3,4-trimethoxybenzyl) piperazine dissolved in 100 ml of methylene chloride. After the reaction mixture has been left at room temperature for the night it is washed with water and then sodium hydroxide solution and then again with water. The whole is dried over magnesium sulphate and evaporated to obtain 65.8 g of the expected product in the form of an oil.

2) Preparation of the amine of formula:

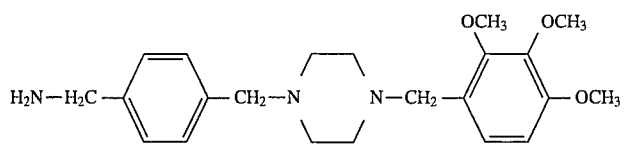

21 ml of borane-dimethyl sulfide are added dropwise, over a period of approximately 15 minutes, to 10 g (0.0278 mol) of the product obtained in the preceding Step dissolved in 280 ml of tetrahydrofuran. The whole is refluxed for one night, allowed to cool, then solvolysed with 43.7 ml of methanol containing a few drops of sulphuric acid. After refluxing for 4 hours, the whole is evaporated to dryness, taken up in methylene chloride, washed with water and dried over $MgSO_4$. Evaporation yields 5 g of the expected product in the form of an oil.

3) Preparation of the compound of formula:

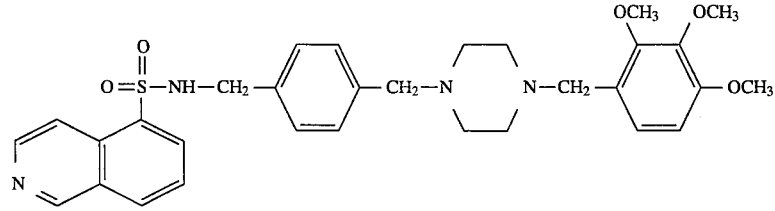

The amine obtained above [15 g (0.014 mol)] is condensed with (isoquinolin-5-yl)sulfochloride hydrochloride in accordance with the method described in Example 1, paragraph 5), to yield the expected compound after purification by chromatography on a silica column using $CH_2Cl_2$/$CH_3OH$ (95:5) as eluant and obtain 2.4 g of pure compound.

4) Preparation of the title compound:

2.4 g (0.0041 mol) of the compound obtained above are treated in accordance with the method of operation described in Example 1, paragraph 6). After purification by flash chromatography on silica using $CH_2Cl_2$/$CH_3OH$ (95:5) as eluant, 2.1 g of free base are obtained which are treated with 3.5 ml of 3.5N ethereal hydrogen chloride to yield the trihydrochloride of the title compound, m.p. 220°–222° C.

EXAMPLE 16

PHARMACOLOGICAL STUDY

The cardiac protecting activity of the products of the present invention was demonstrated:

in vitro
 on the one hand on isolated rats' hearts subjected to a cycle of hypoxia and reoxygenation as well as on rat cardiac cells subjected to hypoxic necrosis,
 on the other hand on an excess intracellular calcium model: the necrosis of rat cardiac cells induced by calcium paradox, and
in vivo
 in the course of myocardial ischaemia episodes induced by coronary stenosis in pigs.

A - IN VITRO STUDY

1 - MATERIALS AND METHOD 1.1. - Hypoxia-reoxygenation in isolated rats' hearts

The hearts of male Wistar rats (325–375 g - Charles River breed) anaesthetized by the intraperitoneal route with sodium pentobarbital (30 mg/kg i.p.) are removed after the i.v. injection of heparin (1 ml/kg), and rapidly perfused according to Langendorffs technique at a constant pressure of 76 mmHg and electrically stimulated at 5 Hz using platinum electrodes. The isovolumetric contractions are recorded by way of a polyethylene balloon which is connected to a pressure sensor (P23- Gould) and introduced into the left ventricle in such a manner as to obtain a diastolic pressure of approximately 10 mmHg.

The physiological solution used, maintained at 37° C., has the following composition (mM): NaCl, 118; KCl, 4.7; $KH_2PO_4$, 1.2; $MgCl_2$, 1.2; $CaCl_2$, 1.3; $NaHCO_3$, 25; glucose, 8; pH 7.4; 95% $O_2$+5% $CO_2$.

After a period of stabilisation of 20 to 30 minutes, the heart is subjected to a 60 minute hypoxia (carried out with 95% $N_2$+5% $CO_2$, $PO_2$<60 mmHg) followed by 30 minutes' reoxygenation; the compound to be tested is incubated 15 minutes beforehand and for the duration of the hypoxia.

For the ex-vivo experiments, the compound is administered by the oral route, (1 ml/kg) 3 hours before the animal is sacrificed.

1.2, - Studies on rat cardiac cells

Primary cultures of cardiomyocytes are produced from the hearts of newly born rats. The cardiac cells are used between the fourth and sixth days after being placed in culture.

1.2.1. Necrosis of rat cardiac cells induced by hypoxia

The cells subjected to hypoxia are incubated for 3 or 4 hours under nitrogen in a pressure chamber maintained at 37° C. The cells are treated with the test molecules only at the time when they are subjected to hypoxia. The cellular necrosis induced by the hypoxia is evaluated by measuring spectrophotometrically the cellular percentage of lactate dehydrogenase liberated in the supernatant after 3 or 4 hours' incubation.

1.2.2. Necrosis of rat cardiac cells induced by calcium paradox

The cardiac cells are first of all incubated for 30 minutes in a buffer without either calcium or magnesium but supplemented by 1 mM EDTA. After removal of the supernatant, the cells are then incubated for 4 hours in a 3.8 mM calcium buffer. The cells are treated twice with the test molecules: at the time of introduction into the EDTA buffer then on transfer into 3.8 mM $Ca^{2+}$ buffer.

2 - RESULTS 2.1. Effects on isolated rats' hearts subjected to hypoxia-reoxygenation Table 1 shows that the compounds of the invention, at the concentrations used ($10^{-6}$M, $3 \times 10^{-7}$M or $5 \times 10^{-7}$M), reduce the contracture developing after 60 minutes' hypoxia from 20% to 63% and from 35% to 95% after 30 minutes' reoxygenation. They furthermore allow improved recovery of function of the hearts during the course of the reoxygenation: the ventricular pressure of the treated hearts in fact reaches from 48% to 89.7% of its initial value before hypoxia, whilst that of the ;control hearts remains restricted to from 22.5% to 33.5% of its initial value.

Table 2 shows that, by comparison with the hearts originating from the control animals, the hearts originating from rats treated by the oral route with the compound of Example 2 are protected against modifications induced by a hypoxia-reoxygenation carried out ex vivo:

1. reduction of the contracture that has developed after 60 minutes' hypoxia and 30 minutes reoxygenation is 50% and 37% respectively compared with that developed by the hearts of the control animals:
2. recovery of the Ventricular pressure (56% of its initial value) is superior to that of the hearts of the control animals (33.5% of its initial value).

TABLE 2

Effect of the compound of Example 2, administered by the oral route to rats, on the contracture and recovery of function of isolated hearts subjected ex vivo to a hypoxia-reoxygenation.

| Compound | n | Contracture (mmHg) | | Left ventricular pressure % of the initial value before hypoxia |
|---|---|---|---|---|
| | | Hypoxia 60 min | Reoxygenation 30 min | Reoxygenation 30 min |
| Control | 5 | 47.6 ± 2.4 | 19.2 ± 4.8 | 33.5 ± 8.2 |
| Example 2 10 mg/kg PO | 7 | 23.7 ± 6.1 | 12.0 ± 6.6 | 56.6 ± 7.6 |

2.2. - Studies on cardiac cells 2.2.1. - Effects on the necrosis of rat cardiac cells induced by hypoxia Table 3 shows that the compounds of the invention reduce hypoxic necrosis in a concentration-dependent manner from a concentration of $10^{-6}$M. The maximum protection varies from 49.4 to 76.4% depending on the compounds.

TABLE 3

Necrosis of rat cardiac cells induced by hypoxia

| Compounds | Concentration (M) | | | |
|---|---|---|---|---|
| | 0 | $10^{-6}$ | $10^{-5}$ | $10^{-4}$ |
| Example 2 | 100 | 56.8 | 23.6 | 47.1 |
| Example 10 | 100 | 83.2 | 91.6 | 46.5 |
| Example 15 | 100 | 75.7 | 67.7 | 50.6 |

The results are expressed as a percentage in relation to the necrosis of the cells induced by hypoxia alone (necrosis index 100).

2.2.2 - Effects on the necrosis of rat cardiac cells induced by calcium paradox

Table 4 shows that the compounds limit necrosis induced by calcium paradox. The maximum protection reaches 70 to 93% at concentrations of $10^{-6}$M or $10^{-5}$M.

TABLE 1

Effects of the compounds of the invention on the contracture and the recovery of function of isolated rats' hearts subjected to a hypoxia-reoxygenation.

| Compounds | Concentration (M) | n | Contracture (mmHg) | | Left ventricular pressure % of the initial value before hypoxia |
|---|---|---|---|---|---|
| | | | Hypoxia 60 min | Reoxygenation 30 min | Reoxygenation 30 min |
| Control | | 7 | 48.0 ± 7.1 | 29.3 ± 8.0 | 33.5 ± 8.2 |
| Example 1 | $10^{-6}$ | 8 | 32.3 ± 1.6 | 7.8 ± 3.4 | 72.4 ± 9.4 |
| Control | | 12 | 50.2 ± 4.6 | 27.7 ± 4.6 | 22.5 ± 6.2 |
| Example 10 | $5 \times 10^{-7}$ | 3 | 18.7 ± 5.8 | 1.3 ± 1.3 | 89.7 ± 11.8 |
| Example 15 | $3 \times 10^{-7}$ | 5 | 40.0 ± 6.2 | 18.0 ± 7.2 | 48.1 ± 4.9 |

TABLE 4

| | Necrosis of rat cardiac cells induced by calcium paradox | | | |
|---|---|---|---|---|
| | Concentration (M) | | | |
| Compounds | 0 | $10^{-7}$ | $10^{-6}$ | $10^{-5}$ |
| Example 2 | 100 | 70.8 | 30.1 | 35.3 |
| Example 15 | 100 | 103.7 | 15.7 | 6.8 |

The results are expressed as a percentage in relation to the necrosis of cells induced by calcium paradox alone (necrosis index 100).

B - IN VIVO STUDY

1 - MATERIALS AND METHODS

The study is carried out on "Large White" pigs of both sexes, aged 3 months and weighing from 18 to 23 kg.

The animals are anaesthetized with Zoletil® (15 mg/kg i.m.). The anaesthesia is maintained by perfusion of 6 to 8 mg/kg/h of sodium thiopental.

They are immediately intubated and ventilated with a mixture of air +$O_2$.

A "T" thoracotomy is carded out by longitudinal section of the sternum and incision between the 4th and 5th rib.

The heart is suspended in a pericardiac cradle by cutting the pericardium and fixing at four points to the thoracic muscles.

An electromagnetic flow ring is positioned at the level of the anterior interventricular branch of the left coronary and a pneumatic balloon is placed immediately downstream of that ring, the two being designed to effect coronary stenosis by flow control. Piezo-electric crystals connected to a Triton sonomicrometer are implanted in the subendocardium of the left ventricular wall according to a circumferential plane perpendicular to the cardiac axis. Those crystals are for the purpose of recording endocardiac EGGs in the region supplied by the stenosed coronary artery.

2- EXPERIMENTAL PROTOCOL

Myocardial ischaemia is effected by inflating the balloon, inducing a reduction in coronary flow of 50 to 60%.

Two identical stenoses of 3 minutes with reproducible and reversible effects are carried out, separated by a recovery interval of 55 minutes.

The treatment is administered by a 5-minute perfusion by the venous route 10 minutes before the stenosis:
perfusion of solvent before the first stenosis
perfusion of product or solvent before the second stenosis.

3 - PARAMETER STUDIED

The modification of the endocardial ECGs in the ischaemic zone consists in an increase in the ST segment measured in millivolts (mV).

4 - RESULTS

The two coronary stenoses carried out in the control group induce the same electrocardiographic modifications. The compounds of the invention administered by the intravenous route at doses of 1 or 3 mg/kg before the second coronary stenosis reduce by 48% to 66% the increase of the ST segment of the endocardiac electrocardiograms compared with the effect of the first coronary stenosis.

| | Endocardiac ST increase (mV) | |
|---|---|---|
| Compounds | Stenosis 1 | Stenosis 2 |
| Control | 1.9 | 1.9 |
| Example 2  1 mg/kg | 1.5 | 0.6 |
| Control | 2.8 | 2.9 |
| Example 10  3 mg/kg | 2.5 | 1.3 |
| Example 15  3 mg/kg | 1.5 | 0.5 |

We claim:

1. A substituted sulfonamide selected from those of formula I:

$$A-\underset{\underset{O}{\|}}{\overset{\overset{O}{\|}}{S}}-\underset{R_1}{N}-D-N\underset{\diagdown\underline{\quad}\diagup}{\overset{\diagup\overline{\quad}\diagdown}{N}}-CH_2-\underset{}{\text{Ar}}(OCH_3)_3 \quad (I)$$

where the aryl group bears three $OCH_3$ substituents.

wherein:

A represents

[various ring systems: isoquinolinyl, benzoxadiazolyl, benzothiadiazolyl, chromonyl (benzopyranonyl), and bicyclic (camphor-type) groups with $CH_2-$ linkers bearing =O, OH, or OH and $CH_2-COOH$]

$R_1$ represents:
  a) hydrogen,
  b) straight-chain alkyl having 1 to 7 carbon atoms inclusive, unsubstituted or substituted by a methyl, phenyl, pyridyl or thienyl, which are each unsubstituted or substituted either by a halogen or by hydroxy,
  c) alkenyl having 3 to 7 carbon atoms inclusive, or
  d) alkynyl having 3 to 7 carbon atoms inclusive; and D represents:
  a) a saturated linear hydrocarbon chain having 2 to 6 carbon atoms inclusive interrupted by one or more oxygen or sulphur or by a cyclopropane or substituted by a gem-dimethyl; or b)

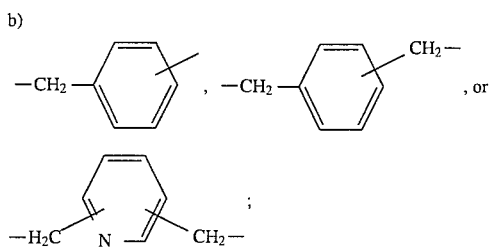

and physiologically-tolerable acid addition salts thereof.

2. A compound of claim 1, which is selected from N-benzyl-N-{3,3-dimethyl-4-[4-(2,3,4-trimethoxybenzyl)piperazin-1-yl]butyl}-(isoquinolin-5-yl)sulfonamide and its fumarate.

3. A compound of claim 1, which is selected from N-(pyrid-3-ylmethyl)-N-{3,3-dimethyl-4-[4-(2,3,4-trimethoxybenzyl)piperazin-1-yl]butyl}-(isoquinolin-5-yl)sulfonamide and its tetrahydrochloride.

4. A compound of claim 1, which is selected from N-ethyl-N-{{4-[4-(2,3,4-trimethoxybenzyl) piperazin-1-yl]methyl}benzyl}(isoquinolin-5-yl)sulfonamide and its trihydrochloride.

5. A pharmaceutical composition useful in the treatment of myocardial ischaemic pathologies, cerebral vascular accident and manifestations of deficiency associated with chronic cerebral circulatory, disorders, comprising as active ingredient an effective amount of a compound of claim 1, in combination with one or more pharmaceutically acceptable excipients.

6. A method for treating a living animal body afflicted with a condition selected from myocardial ischaemic pathology, cerebral vascular accident, or a manifestation of deficiency associated with a chronic cerebral circulatory disorder, comprising the step of administering to the said living animal body an amount of a substituted sulfonamide selected from those of formula I:

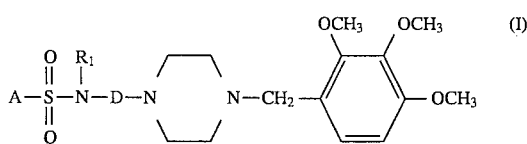

wherein:

A represents:

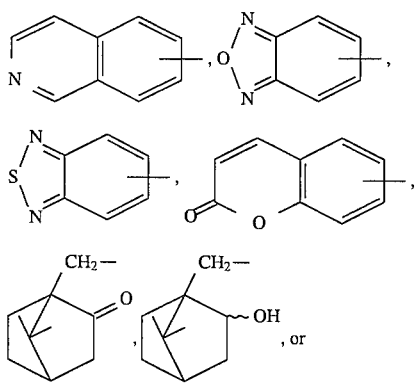

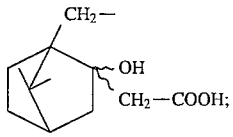

$R_1$ represents:
  a) hydrogen,
  b) straight-chain alkyl having 1 to 7 carbon atoms inclusive, unsubstituted or substituted by a methyl, phenyl, pyridyl or thienyl, which are each unsubstituted or substituted either by a halogen or by hydroxy,
  c) alkenyl having 3 to 7 carbon atoms inclusive, or
  d) alkynyl having 3 to 7 carbon atoms inclusive, and D represents:
  a) a saturated linear hydrocarbon chain having 2 to 6 carbon atoms inclusive interrupted by an oxygen or sulphur or by a cyclopropane or substituted by a gem-dimethyl; or
b)

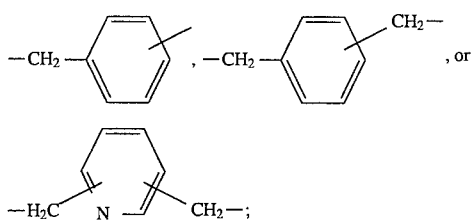

and physiologically-tolerable acid addition salts thereof, which is effective for the alleviation of the said condition.

7. A method of claim 6 wherein the compound is selected from N-benzyl-N-{3,3-dimethyl-4-[4-(2,3,4-trimethoxybenzyl) piperazin-1-yl]butyl}-(isoquinolin-5-yl)sulfonamide and its fumarate.

8. A method of claim 6 wherein the compound is selected from N-(pyrid-3-ylmethyl)-N-{3,3-dimethyl-4-[4-(2,3,4-trimethoxy-benzyl)piperazin-1-yl]butyl}-(isoquinolin-5-yl) sulfonamide and its tetrahydrochloride.

9. A method of claim 6 wherein the compound is selected from N-ethyl-N-{{4-[4-(2,3,4-trimethoxybenzyl)piperazin-1-yl]methyl}-benzyl}-(isoquinolin-5-yl}sulfonamide and its trihydrochloride.

10. A method of claim 6, wherein the compound is selected from the group consisting of:

N-{3-[4-(2,3,4-trimethoxybenzyl)piperazin-1-yl]propyl}-(isoquinolin-5-yl)sulphonamide N-{4-[4-(2,3,4-trimethoxybenzyl)piperazin-1-yl]butyl}-(isoquinolin-5-yl)sulphonamide N-{2-[4-(2,3,4-trimethoxybenzyl)piperazin-1-yl]ethyl}-(isoquinolin-5-yl)sulphonamide N-methyl-N-{3-[4-(2,3,4-trimethoxybenzyl)piperazin-1-yl] propyl}-(isoquinolin-5-yl)sulphonamide N-methyl-N-{4-[4-(2,3,4-trimethoxybenzyl)piperazin-1-yl] butyl}-(isoquinolin-5-yl)sulphonamide N-ethyl-N-{4-[4-(2,3,4-trimethoxybenzyl)piperazin-1-yl] butyl}-(isoquinolin-5-yl)sulphonamide N-ethyl-N-{2-[4-(2,3,4-trimethoxybenzyl)piperazin-1-yl] ethyl}-(isoquinolin-5-yl)sulphonamide N-methyl-N-{2-[4-(2,3,4-trimethoxybenzyl)piperazin-1-yl] ethyl}-(isoquinolin-5-yl)sulphonamide N-ethyl-N-{3-[4-(2,3,4-trimethoxybenzyl)piperazin-1-yl] propyl}-(isoquinolin-5-yl)sulphonamide N-propyl-N-{4-[4-(2,3,4-trimethoxybenzyl)piperazin-1-yl] butyl}-(isoquinolin-5-yl)sulphonamide N-propargyl-N-{4-[4-(2,3,4-trimethoxybenzyl)piperazin-1-yl]butyl}-(isoquinolin-5-yl)sulphonamide N-butyl-N-{4-[4-(2,3,4-trimethoxybenzyl)piperazin-1-yl]butyl}-(isoquinolin-5-yl)sulphonamide N-isobutyl-N-{4-[4-(2,3,4-trimethoxybenzyl)piperazin-1-yl]butyl}-(isoquinolin-5-yl)sulphonamide N-benzyl-N-{4-[4-(2,3,4-trimethoxybenzyl)piperazin-1-yl]butyl}-(isoquinolin-5-yl)sulphonamide, and N-allyl-N-{4-[4-(2,3,4-trimethoxybenzyl)piperazin-1yl] butyl}-(isoquinolin-5-yl)sulphonamide, and pharmaceutically-acceptable acid addition salts thereof.

11. A substituted sulfonamide selected from the group consisting of:

N-{3-[4-(2,3,4-trimethoxybenzyl)piperazin-1-yl]propyl}-(isoquinolin-5-yl)sulphonamide N-{4-[4-(2,3,4-trimethoxybenzyl)piperazin-1-yl]butyl}-(isoquinolin-5-yl)sulphonamide N-{2-[4-(2,3,4-trimethoxybenzyl)piperazin-1-yl]ethyl}-(isoquinolin-5-yl)sulphonamide N-methyl-N-{3-[4-(2,3,4-trimethoxybenzyl)piperazin-1-yl]propyl}-(isoquinolin-5-yl)sulphonamide N-methyl-N-{4-[4-(2,3,4-trimethoxybenzyl)piperazin-1-yl]butyl}-(isoquinolin-5-yl)sulphonamide N-ethyl-N-{4-[4-(2,3,4-trimethoxybenzyl)piperazin-1-yl] butyl}-(isoquinolin-5-yl)sulphonamide N-ethyl-N-{2-[4-(2,3,4-trimethoxybenzyl)piperazin-1-yl] ethyl}-(isoquinolin-5-yl)sulphonamide N-methyl-N-{2-[4-(2,3,4-trimethoxybenzyl)piperazin-1-yl]ethyl}-(isoquinolin-5-yl)sulphonamide N-ethyl-N-{3-[4-(2,3,4-trimethoxybenzyl)piperazin-1-yl] propyl}-(isoquinolin-5-yl)sulphonamide N-propyl-N-{4-[4-(2,3,4-trimethoxybenzyl)piperazin-1-yl]butyl}-(isoquinolin-5-yl)sulphonamide N-propargyl-N-{4-[4-(2,3,4-trimethoxybenzyl)piperazin-1yl] butyl}-(isoquinolin-5-yl)sulphonamide N-butyl-N-{4-[4-(2,3,4-trimethoxybenzyl)piperazin-1-yl]butyl}-(isoquinolin-5-yl)sulphonamide N-isobutyl-N-{4-[4-(2,3,4-trimethoxybenzyl)piperazin-1-yl]butyl}-(isoquinolin-5-yl)sulphonamide N-benzyl-N-{4-[4-(2,3,4-trimethoxybenzyl)piperazin-1-yl]butyl}-(isoquinolin-5-yl)sulphonamide, and N-allyl-N-{4-[4-(2,3,4-trimethoxybenzyl)piperazin-1-yl] butyl}-(isoquinolin-5-yl)sulphonamide, and pharmacologically-acceptable acid addition salts thereof.

12. A pharmaceutical composition useful in the treatment of myocardial ischaemic pathologies, cerebral vascular accident and manifestations of deficiency associated with chronic cerebral circulatory disorders, comprising as active ingredient an effective amount of a compound of claim 11, in combination with one or more pharmaceutically-acceptable excipients.

* * * * *

UNITED STATES PATENT AND TRADEMARK OFFICE
CERTIFICATE OF CORRECTION

PATENT NO. : 5,565,457
DATED : Oct. 15, 1996
INVENTOR(S) : J. Peglion; J. Vilaine; N. Villeneuve; J. Iliou; J. Bidouard It is certified that error appears in the above-indentified patent and that said Letters Patent is hereby corrected as shown below:

Column 1, line 53: "ting" should read -- ring --.

Column 2, line 2: Delete the number "2" before the word "Patent".

Column 3, line 4: "convened" should read -- converted --

Column 6, line 58: "cyclopropyhnethyl}-" should read -- cyclopropylmethyl}- --.

Column 7, line 28: "B.p./$_{5mm}$ =" should read -- B.p./$_{15mm}$ = --.

Column 9, line 13: Delete excessive space in the line.

Column 9, line 39: "sing." at beginning of line should read -- stirring. --.

Column 9, line 42: "carded" should read -- carried --.

Column 11, line 59: Delete the "-" (dash) at the end of the line and Insert -- ) --.

Column 11, line 60: Delete the ")" from the beginning of the line.

UNITED STATES PATENT AND TRADEMARK OFFICE
CERTIFICATE OF CORRECTION

PATENT NO. : 5,565,457
DATED : Oct. 15, 1996
INVENTOR(S) : J. Peglion; J. Vilaine; N. Villeneuve; J. Iliou; J. Bidouard It is certified that error appears in the above-indentified patent and that said Letters Patent is hereby corrected as shown below:

Column 14, line 1: in vitro" should read -- _in vitro_ --.

Column 14, line 8: in vivo" should read -- _in vivo_ --.

Column 14, line 28: "Langendorffs" should read -- Langendorff's --.

Column 15, line 39: "Ventricular" should read -- ventricular --.

Column 18, line 61: Delete "one or more" and Insert -- a --.

Column 19, lines 14 & 15: Delete excessive space in these two lines.

UNITED STATES PATENT AND TRADEMARK OFFICE
CERTIFICATE OF CORRECTION

PATENT NO. : 5,565,457
DATED : Oct. 15, 1996
INVENTOR(S) : J. Peglion; J. Vilaine; N. Villeneuve; J. Iliou; J. Bidouard It is certified that error appears in the above-indentified patent and that said Letters Patent is hereby corrected as shown below:

Column 19, line 30: Delete the "," (comma) after "circulatory".

Column 19, line 32: Insert a -- - -- (dash) between "pharmaceutically" and "acceptable".

Signed and Sealed this

Twenty-eighth Day of January, 1997

Attest:

BRUCE LEHMAN

Attesting Officer    Commissioner of Patents and Trademarks